United States Patent [19]

Mundt

[11] Patent Number: 4,923,817
[45] Date of Patent: May 8, 1990

[54] FERMENTER FOR CULTURING CELL CULTURES

[75] Inventor: Wolfgang Mundt, Vienna, Austria

[73] Assignee: "Immuno" Aktiengesellschaft fur Chemisch-Medizinische, Produkte, Fed. Rep. of Germany

[21] Appl. No.: 273,931

[22] Filed: Nov. 21, 1988

[30] Foreign Application Priority Data

Nov. 23, 1987 [DE] Fed. Rep. of Germany ....... 3739650

[51] Int. Cl.$^5$ .............................................. C12M 1/06
[52] U.S. Cl. .................... 435/315; 435/313; 435/291; 435/287; 422/135; 422/225
[58] Field of Search ............... 435/315, 291, 313, 314, 435/286, 316; 99/323.1, 323.2; 422/135, 225; 261/87, 93

[56] References Cited

U.S. PATENT DOCUMENTS

| | | | |
|---|---|---|---|
| 1,402,248 | 1/1922 | Noe ..................................... | 435/313 |
| 2,542,031 | 2/1951 | Humfeld et al. .................... | 435/291 |
| 4,332,906 | 6/1982 | Taylor ................................. | 435/291 |
| 4,649,114 | 3/1987 | Miltenburger et al. ............. | 435/315 |
| 4,680,267 | 7/1987 | Eppstein et al. .................... | 435/315 |

FOREIGN PATENT DOCUMENTS

| | | |
|---|---|---|
| WO85/02195 | 11/1984 | European Pat. Off. . |
| WO87/05322 | 3/1987 | European Pat. Off. . |
| 1604693 | 1/1972 | France . |
| 2393535 | 6/1977 | France . |
| 2559500 | 2/1984 | France . |
| 1331887 | 10/1984 | U.S.S.R. . |

OTHER PUBLICATIONS

*The Large-Scale Cultivation of Mammalian Cells*, Scientific American, vol. 248, No. 1, pp. 24–31 (1/83).

Primary Examiner—Larry Jones
Attorney, Agent, or Firm—Saidman, Sterne, Kessler & Goldstein

[57] ABSTRACT

A fermenter for culturing cell cultures, and particularly on microcarriers. The fermenter comprises a vessel in which the cell cultures are maintained in suspension by means of an agitator. A screen aerator supplies oxygen in finely distributed form to the suspension at a distance away from the rotating axis of the agitator.

14 Claims, 3 Drawing Sheets

FERMENTER FOR CULTURING CELL CULTURES

DESCRIPTION

The invention relates to a fermenter for culturing cell cultures, more particularly on microcarriers, the fermenter comprising: a vessel in which the cell cultures are maintained in suspension by means of an agitator; and an aerator for supplying oxygen in finely distributed form to the suspension at a distance from and eccentrically of the agitation axis.

Conventionally, cell cultures for culturing are placed on microcarriers on which the cultures are suspended in a liquid in the fermenter. Oxygen, usually in the form of air, is supplied to boost the growth of the cell cultures.

Originally, the air was simply introduced in the bottom part of the fermenter. However, the rising air bubbles led to foaming and, therefore, to destruction of the cells on the top microcarriers.

In endeavours to obviate destruction of the cell cultures, passive oxygen enrichment was tried, the fermenter vessel being made frustum-shaped so that the suspension surface in contact with the ambient air was increased. However, the oxygen uptake in the process was unsatisfactory.

Earlier endeavours to carry out oxygen enrichment in separate vessels or to inject the oxygen into the suspension through a screen have not always led to the required result.

Starting from the latter endeavour, a cylindrical screen cage was fitted centrally in the fermenter vessel and baffle plates disposed on an axially oscillating shaft and formed with conical passages were placed in the cage. The conical passages are disposed in opposite directions to one another on each plate so that the oscillatory movements of the plates produce pumping movements between adjacent conical passages. The oxygen introduced into the cage through the shaft is distributed very finely and almost dissolved because of the resulting shear flows. The foaming associated with the earlier processes is therefore obviated. However, the oxygen uptake of the suspension is still too low. Also, the agitator present in any fermenter must now be driven from below. A shaft must therefore extend through the vessel base, leading to sealing problems and more particularly to a back-up of microcarriers between the centre of the agitator vane and the vessel base, with a resulting destruction of cell cultures.

Finally, DE No. 3 504 748 C2 discloses a fermenter of the kind hereinbefore set out wherein the aerator is in the form of an air tube having a filter and a porous outlet member extending directly into the suspension. The porous outlet member is disposed between the vessel wall and the outer orbit of the agitator relatively close thereto. In practice, direct oxygen injection into the suspension in this way is possible only with encapsulated cells. Consequently, spherical capsules which have a semipermeable diaphragm and in which the cells are disposed are used in the known fermenter. When dealing with encapsulated cells, the agitator can run at such a high speed that the gas bubbles introduced directly into the suspension are broken up so that the oxygen is mixed uniformly in the suspension. In the fermenter disclosed by DE No. 3 504 748, the only reason for the aerator being disposed eccentrically outside the agitator is that there is no room for the agitator at the centre of the vessel since the agitator is disposed there.

It is the object of the invention to provide a fermenter which, using simple constructional means, can provide intensive growth of even very delicate cell cultures.

According to the invention, therefore, in a fermenter of the kind hereinbefore set out the aerator is disposed near the edge of the vessel and is devised as a screen aerator having a screen in the form of a hollow member which is adapted to be supplied with the oxygen through a central shaft.

In the fermenter according to the invention the oxygen-containing gas is supplied to the suspension by way of a aerator—i.e. indirectly. There are no cell cultures in the hollow member formed by the screen and so there is no risk of foaming. The eccentric arrangement of the or each aerator near the vessel edge increases the input of oxygen into the suspension to a surprisingly high extent. At the place of the aerator arrangement, the suspension rotated by the agitator is in a state of high flow velocity, so that the oxygen-enriched liquid is washed rapidly out of each hollow member screen and mixed with the remainder of the suspension. This feature solves the problem found in conventional screen aerators of very rapid oxygen saturation occuring in this screen, so that increased oxygen feed to the screen does not lead to increased oxygen uptake. The invention therefore deliberately uses the kinetic velocity of the suspension, such velocity increasing in agitation towards the vessel edge, to boost indirect oxygen uptake by way of a screen, and this feature is successful although the agitator must run very slowly because of the sensitivity of the cell cultures.

Conveniently, a plurality of baffle plates having a number (plurality) of conical passages are disposed one above another in the screen on a central oscillating shaft connected to a vibratory drive and the shaft is hollow for supplying the oxygen. This step ensures a very intensive introduction of oxygen without foaming.

The pore size of the screen is approximately 100 μm.

In large fermenters, two or more aerators can be distributed around the vessel periphery.

Advantageously, to obviate sealing problems, the drive shaft of the agitator extends downwardly into the vessel.

To provide continuous monitoring of the oxygen partial pressure, a sensor for measuring the oxygen partial pressure of the suspension is disposed in the vessel.

This makes it possible to have accurate control of oxygen uptake since the sensor can be connected to a control facility for controlling the oxygen delivery of the aerator.

When a number of aerators are provided, the same can be stopped at choice, thus providing a simple form of control for oxygen uptake.

The point is that the control can be embodied by the aerators being adapted to be switched on and off in dependence upon the measured oxygen partial pressure.

An embodiment of the invention will be described in greater detail hereafter with reference to the drawings wherein.

Figure 1:
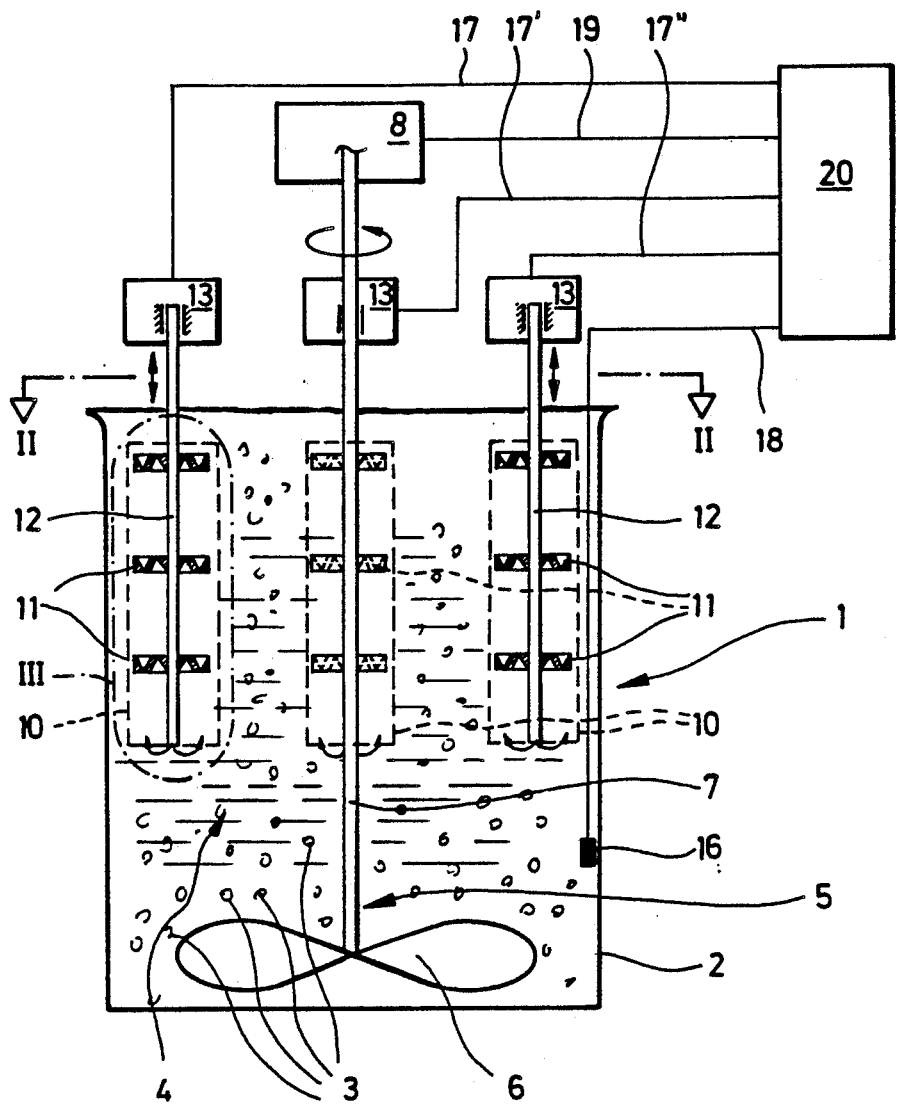
FIG. 1 is a diagrammatic view in vertical section of an embodiment of a fermenter according to the invention.

FIG. 1 shows a fermenter 1 having a vessel 2 which is closed at the top and in which cell cultures are suspended on microcarriers 3 in a liquid 4. The microcarriers in this embodiment are plastics pellets.

The fermenter 1 has an agitator 5 having a vane 6, drive shaft 7 and motor 8. The drive shaft 7 coincides with the agitation axis around which the whirling flow produced by the agitator 5 rotates. The agitator 5 is preferably disposed in the central portion of the vessel.

The fermenter 1 of the embodiment shown here also comprises four aerators 9.

Figure 2:
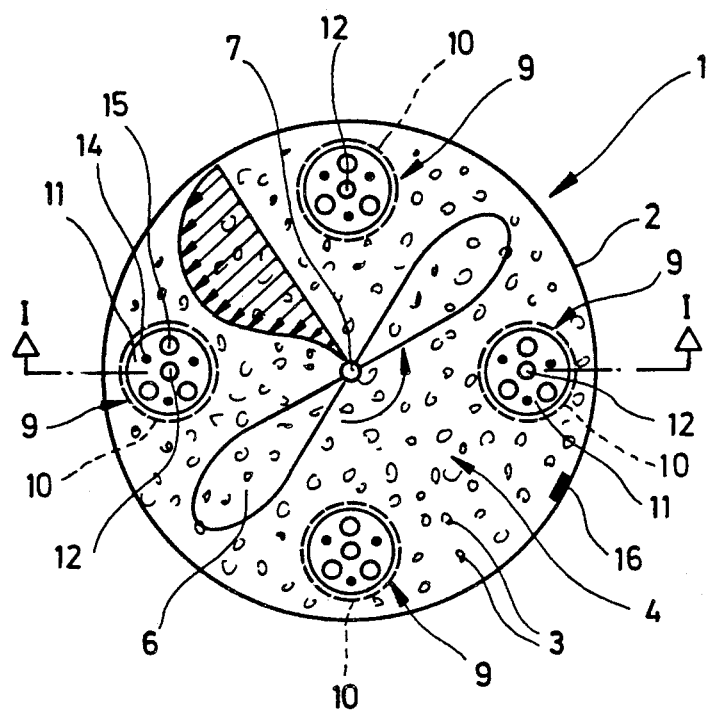
FIG. 2 shows the fermenter looking in the direction of the arrows II of FIG. 1.

As can be gathered particularly clearly from FIG. 2, the aerators 9 are disposed at a distance from and eccentrically of the agitation axis (drive shaft 7). The aerators 9 are disposed close to the edge (peripheral portion) of the vessel 2.

Figure 3:
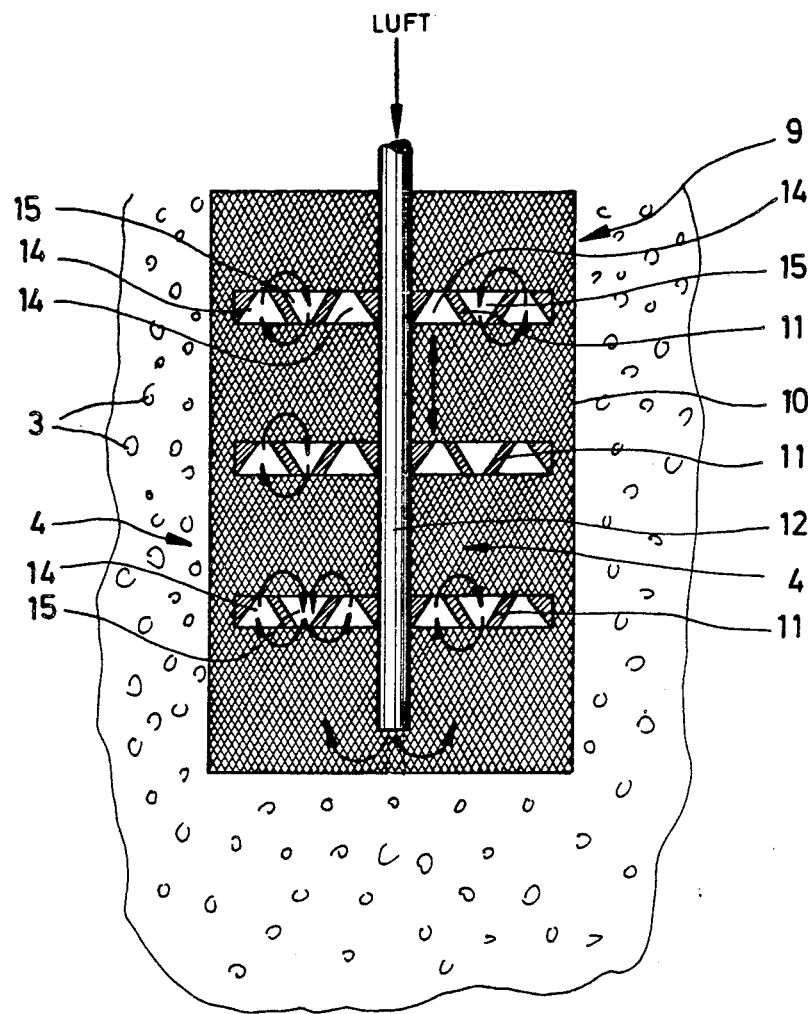
FIG. 3 shows a detail III of the fermenter of FIG. 1.

As can be gathered particularly clearly from FIGS. 1 and 3, the aerators 9 are screen aerators. To this end, an aerator 9 has a screen 10 which is shaped to form a cylindrical hollow member and in which a number of baffle plates 11 are disposed one above another. The plates 11 are interconnected by way of an oscillating shaft 12 disposed axially of the screen 10. Shaft 12 has its top end mounted in a vibratory drive 13 which imparts high-frequency vibrations to the shaft 12 in the axial direction. The shaft 12 transmits these vibrations to the plates 11.

As will be clearly apparent from FIG. 3, the discrete plates 11 have a number of conical passages 14, 15 so disposed that adjacent passages 14, 15 extend towards one another—i.e., a passage 14 narrows upwardly and the adjacent passage 15 narrows downwardly.

The shafts 12 have a hollow interior and are open at the bottom. The oxygen which the aerator 9 is required to mix into the liquid flows through the interior of the shafts 12 as indicated by arrowing and issues at the bottom end of the shafts 12. The rising air bubbles are finely distributed by the plates 11. For the sake of clarity, the air valves and the air-conveying means are not shown.

The pore size of the screen 10 of this embodiment is about 100 μm.

A sensor 16 for measuring the oxygen partial pressure of the suspension is disposed in the vessel 2. The vibratory drives 13, motor 8 and sensor 16 are connected by way of control lines 17, 17', 17'', ..., 18 and 19 to a control facility 20. The same is adapted to switch on and off the motor 8, drives 13 and the air valves (not shown) for introducing air through the shafts 12. Also, the number of aerators in operation can be controlled in dependence upon the oxygen partial pressure measured by the sensor 16.

An embodiment of the process according to the invention will be described in greater detail hereinafter with reference to the fermenter hereinbefore described.

The liquid 4 in which the cell cultures are present on microcarriers 3 is in the vessel 2. The agitator 5 is started so that the vane 6 rotates anticlockwise and keeps the microcarriers 3 in suspension in the liquid 4 (cf. FIG. 2). A whirling flow arises around the agitation axis (drive shaft 7) of the agitator 5. The flow profile of this whirling flow is shown by way of indication in FIG. 2. As will be apparent, the flow velocity near the vessel edge is much higher than at the vessel centre, where flow velocity is negligible. To aerate the suspension in the fermenter 1, oxygen is introduced by means of the aerators 9 in the highest flow velocity zone of the whirling flow just mentioned.

One or more aerators 9 is or are selectively started, depending upon the required partial pressure, to introduce oxygen into the suspension. The air valves (not shown) therefore allow air—i.e. oxygen—to flow through the shafts 12 to the interior of the screens 10. The plates 11 are reciprocated vertically by the drives 13. Liquid 4, but no microcarriers 3, is disposed inside the screens 10. High shear flows can therefore be produced in the screens 10 without any destruction of cell cultures on the microcarriers 3. These high shear flows are produced by the high-frequency reciprocation of the plates 11 and the pumping flow produced by the conical passages 14, 15. Air reaching the aerator 9 is therefore distributed satisfactorily. The air bubbles are chopped up so small that the air is dissolved in the liquid 4. The air thus dissolved mixes rapidly below the suspension outside the aerators 9 because the same are disposed near a relatively rapid flow.

Optimal oxygen perfusion can therefore always be achieved.

I claim:

1. A fermenter for culturing cell cultures on microcarriers in a liquid, said fermenter comprising:
   a vessel having a central portion and a peripheral portion;
   an agitator disposed within said vessel for maintaining the cell culture in a suspension within said vessel, said agitator having an axis for rotation;
   a screen aerator for supplying oxygen in finely distributed form to the suspension within said vessel, said screen aerator having a central shaft and being disposed eccentrically of said axis of said agitator in a zone of high flow velocity and near said peripheral portion of said vessel, said screen aerator having a screen surrounding said central shaft and thereby forming a hollow space, said hollow space being filled with said liquid and being supplied with oxygen through said central shaft, said screen preventing microcarriers from entering said screen aerator.

2. A fermenter according to claim 1, wherein said central shaft is an oscillating shaft formed within said screen aerator and connected to a vibratory drive, said central shaft being hollow for supplying oxygen to the suspension.

3. A fermenter according to claim 2, further comprising a plurality of baffle plates disposed on said central shaft, each of said baffle plates having a plurality of conical passages disposed one above another.

4. A fermenter according to claim 1, further comprising a plurality of baffle plates disposed on said central shaft, each of said baffle plates having a plurality of conical passages disposed one above another.

5. A fermenter according to claim 1, wherein the pore size of said screen is approximately 100 μm.

6. A fermenter according to claim 1, further comprising a second screen aerator, said screen aerator and second screen aerator disposed around said peripheral portion of said vessel.

7. A fermenter according to claim 1, wherein said central shaft extends downwardly into said vessel.

8. A fermenter according to claim 1, further comprising a sensor for measuring the oxygen partial pressure of the suspension, said sensor disposed within said vessel.

9. A fermenter according to claim 1, further comprising a sensor disposed in said vessel and connected to a control facility for controlling the oxygen delivery of said screen aerator.

10. A fermenter according to claim 8, wherein said sensor is connected to a control facility for controlling the oxygen delivery of said screen aerator.

11. A fermenter according to claim 1, further comprising a plurality of said screen aerators, each of said screen aerators is capable of being selectively stopped.

12. A fermenter according to claim 6, wherein each of said screen aerators is capable of being selectively stopped.

13. A fermenter according to claim 11, wherein each of said plurality of screen aerators can be selectively started and stopped based on the measured oxygen partial pressure.

14. A fermenter according to claim 12, wherein each of said plurality of screen aerators can be selectively started and stopped based on the measured oxygen partial pressure.

* * * * *